United States Patent [19]
Lazzara et al.

[11] Patent Number: 5,582,299
[45] Date of Patent: Dec. 10, 1996

[54] DENTAL IMPLANT PACKAGING

[75] Inventors: Richard J. Lazzara, Lake Worth; Keith D. Beaty; Thomas S. Heylmun, both of West Palm Beach, Fla.

[73] Assignee: Implant Innovations, Inc., West Palm Beach, Fla.

[21] Appl. No.: 538,347

[22] Filed: Oct. 3, 1995

Related U.S. Application Data

[63] Continuation of Ser. No. 203,575, Mar. 1, 1994, abandoned.

[51] Int. Cl.⁶ .................................................. B65D 85/20
[52] U.S. Cl. ........................ 206/63.5; 206/438; 206/469
[58] Field of Search ................................... 206/63.5, 368, 206/369, 438, 469, 471; 433/141, 173, 174, 213, 229

[56] References Cited

U.S. PATENT DOCUMENTS

| | | | |
|---|---|---|---|
| 4,444,310 | 4/1984 | Odell | 206/471 |
| 4,671,410 | 6/1987 | Hansson et al. | |
| 4,712,681 | 12/1987 | Bränemark et al. | |
| 4,722,733 | 2/1988 | Howson | 206/471 |
| 4,763,788 | 8/1988 | Jorneus et al. | 206/438 |
| 4,856,648 | 8/1989 | Krueger | |
| 4,978,007 | 12/1990 | Jacobs et al. | 206/469 |
| 5,026,285 | 6/1991 | Durr et al. | 433/141 |
| 5,049,073 | 9/1991 | Lauks | 433/174 |
| 5,062,800 | 11/1991 | Niznick | 206/368 |
| 5,125,840 | 6/1992 | Durr | 433/173 |
| 5,368,160 | 11/1994 | Leuschen et al. | 433/174 |

FOREIGN PATENT DOCUMENTS

| | | | |
|---|---|---|---|
| 0312698 | 4/1989 | European Pat. Off. | 433/173 |
| 1662545 | 7/1991 | U.S.S.R. | 433/213 |

Primary Examiner—Jimmy G. Foster
Attorney, Agent, or Firm—Arnold, White & Durkee

[57] ABSTRACT

A dental implant packaging system for contamination-free packaging, storage, transport and delivery of dental implants and related components. Various embodiments of the system as applied to a dental implant and its cover screw are shown in which a dental implant is housed in a transparent tubular capsule that is lined with a titanium sleeve which covers the head and part of the body of the implant, leaving the tail end exposed to view. The head is restrained in the opening into the capsule and a cap which closes the capsule also serves to hold the head in place.

69 Claims, 3 Drawing Sheets

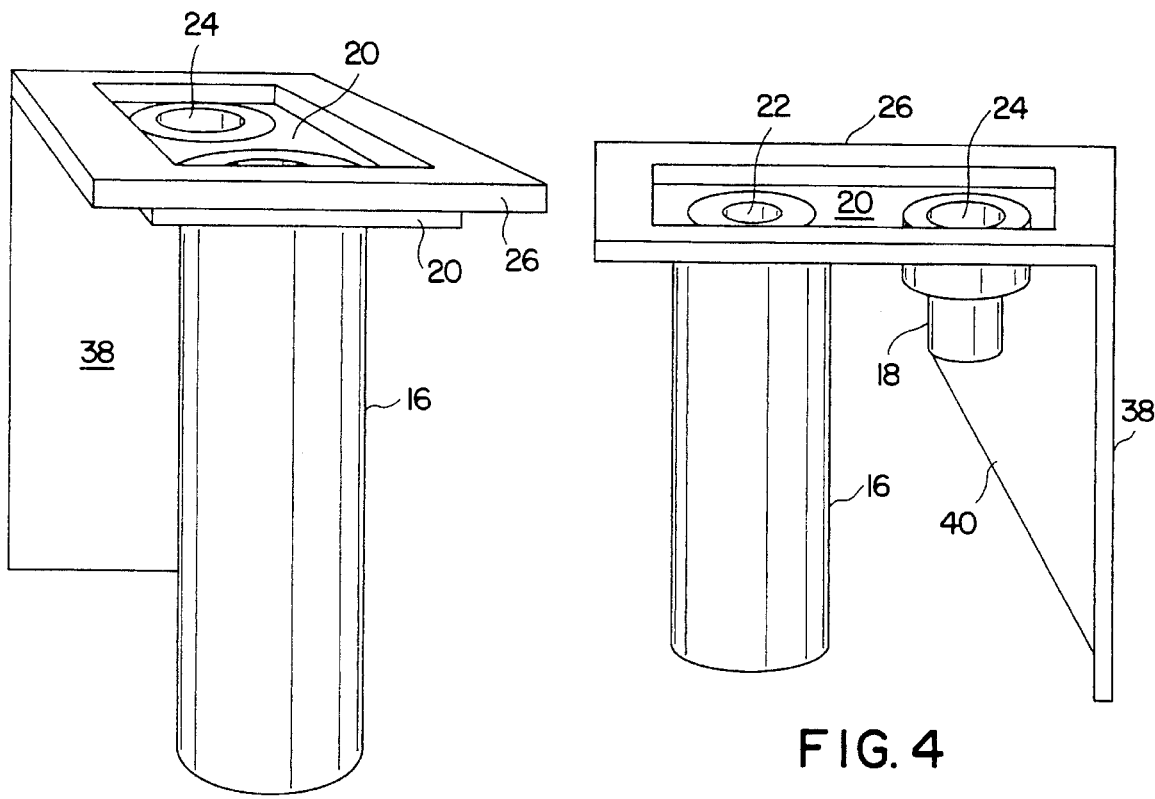
FIG. 3
FIG. 4
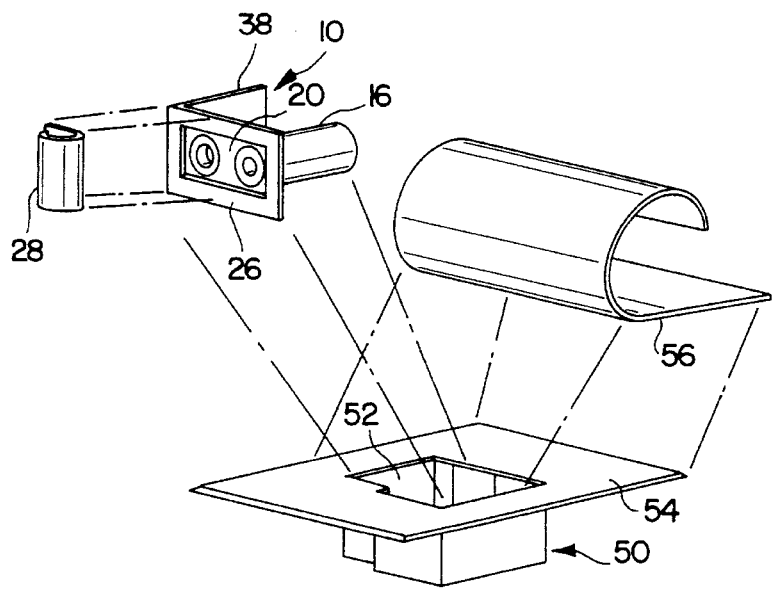
FIG. 5

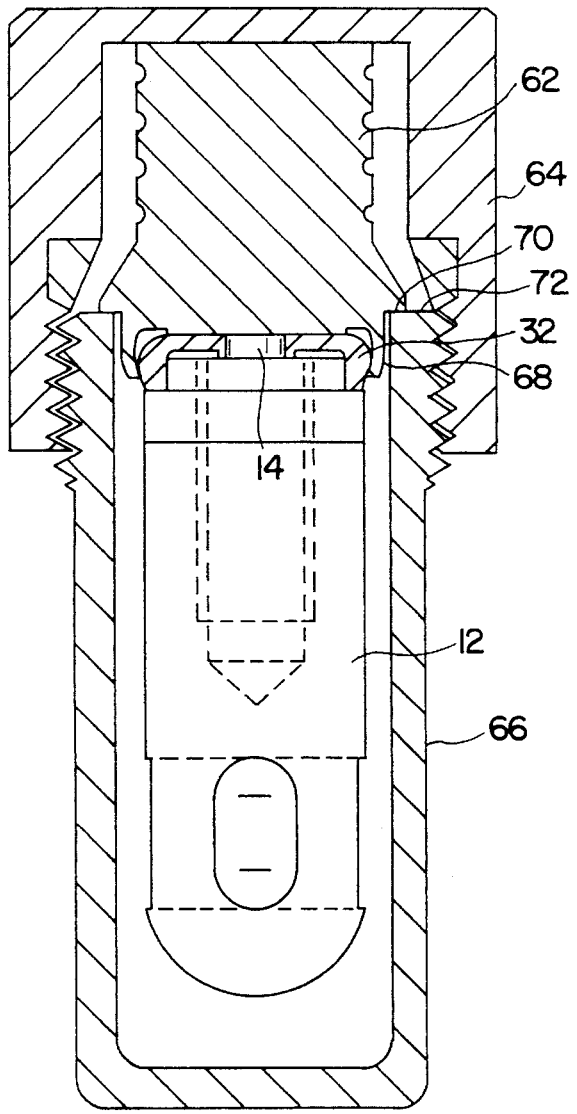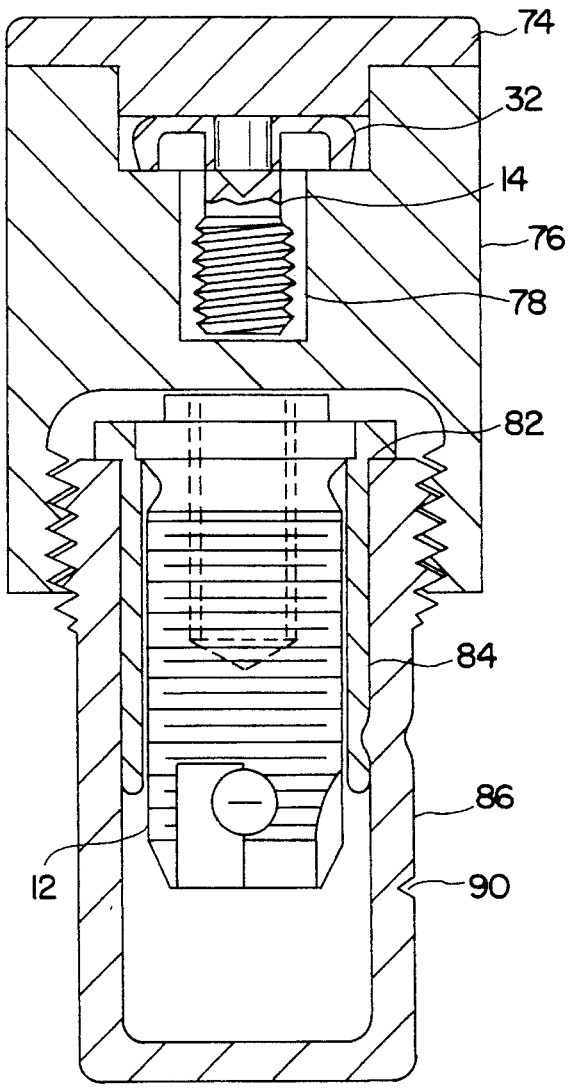
FIG. 6
FIG. 7

DENTAL IMPLANT PACKAGING

This application is a continuation of application Ser. No. 08/203,575, filed Mar. 1, 1994, now abandoned.

BACKGROUND OF THE INVENTION

This invention relates in general to dental implants, and more particularly to contamination-free packaging, storage and transport and delivery of dental implants and related components as a unit for improved convenience to the dental practitioner.

U.S. Pat. No. 5,062,800 describes a dental implant package which includes a two-part handle that can be attached to the implant inside the package, adding the weight and cost of the handle to each package.

U.S. Pat. No. 4,763,788 describes a hermetically-sealed glass capsule enclosing a dental implant in an inner sleeve that is axially longer than the implant and is made of the same material as the implant and is held in place in the capsule by a spring that is also contained in the sealed capsule. This package is opened by breaking the glass capsule.

GENERAL NATURE OF THE INVENTION

According to the present invention in one of its unique aspects a dental implant package has two compartments for simultaneous delivery of a dental implant and a related component, such as a healing screw, to the dental practitioner. In this package the openings to the two compartments are preferably coplanar so that they can be closed with a common cover. To this end each compartment may be attached at its open end to, and open through an aperture in, a relatively stiff substantially planar support, and the common cover may be peripherally sealed to that support. The compartment reserved for the dental implant may contain a sleeve made of the same material as the implant, but owing to the improved design of the present invention that sleeve may be axially shorter than the implant fixture, thereby saving weight and the cost of unnecessary material. The compartment reserved for the related component may be axially shorter than the implant compartment. Desirably, the package includes structural members for holding the two compartments in prescribed relative positions, and to facilitate the handling of the package while the common cover is being removed and the contents are being extracted from their respective compartments.

In a further improvement the invention provides a sealable container for the implant package, which protects the implant package from damage during storage and transport, and provides a second shield against contamination. Conveniently, like the implant package, this container has an open side and may be fitted with a cover that is peripherally sealed to that open side.

In another aspect of the invention the implant compartment is provided with a unique cover. One embodiment of this cover includes storage for a cover screw. Another embodiment includes a holder for releasably grasping a cover screw attached to one end of the implant fixture within the compartment In practicing this aspect of the invention the package may omit the second compartment.

DETAILED DESCRIPTION OF THE INVENTION

The invention is explained in greater detail with reference to the accompanying drawings, in which:

FIG. 3 is an end view of FIG. 1;

FIG. 4 is a partial top view of the other side of FIG. 1;

FIG. 5 is an exploded view of the package of FIG. 1 and a container for that package;

FIG. 6 is a partial longitudinal section view of a second embodiment of the invention; and FIG. 7 is a partial longitudinal section view of a third embodiment of the invention.

Figure 1:
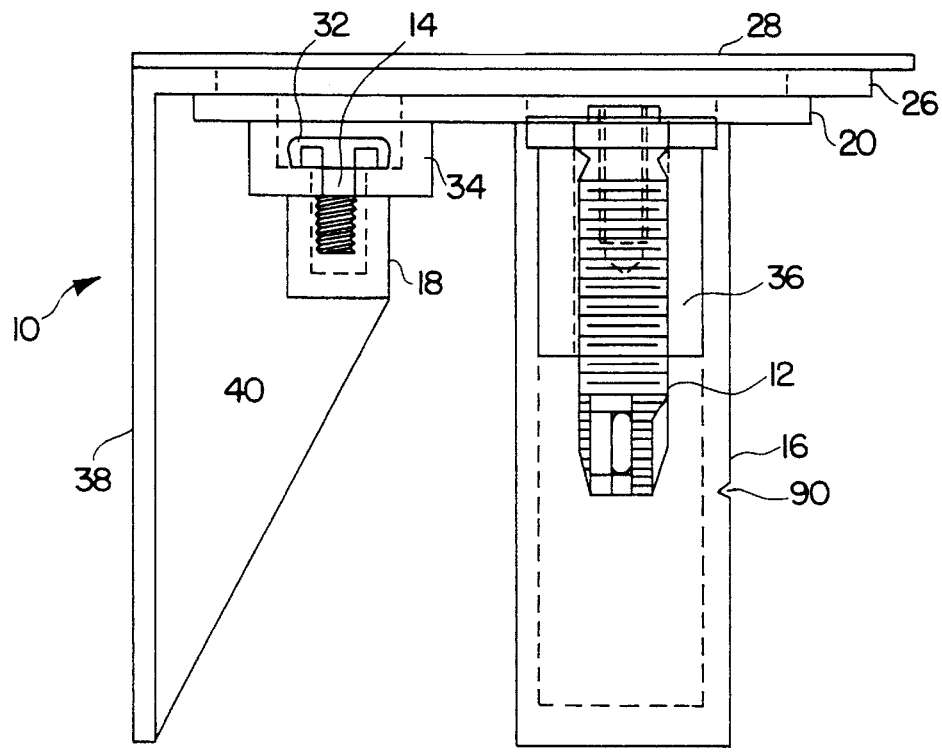
FIG. 1 is a side view of a first embodiment of the invention.
Figure 2:
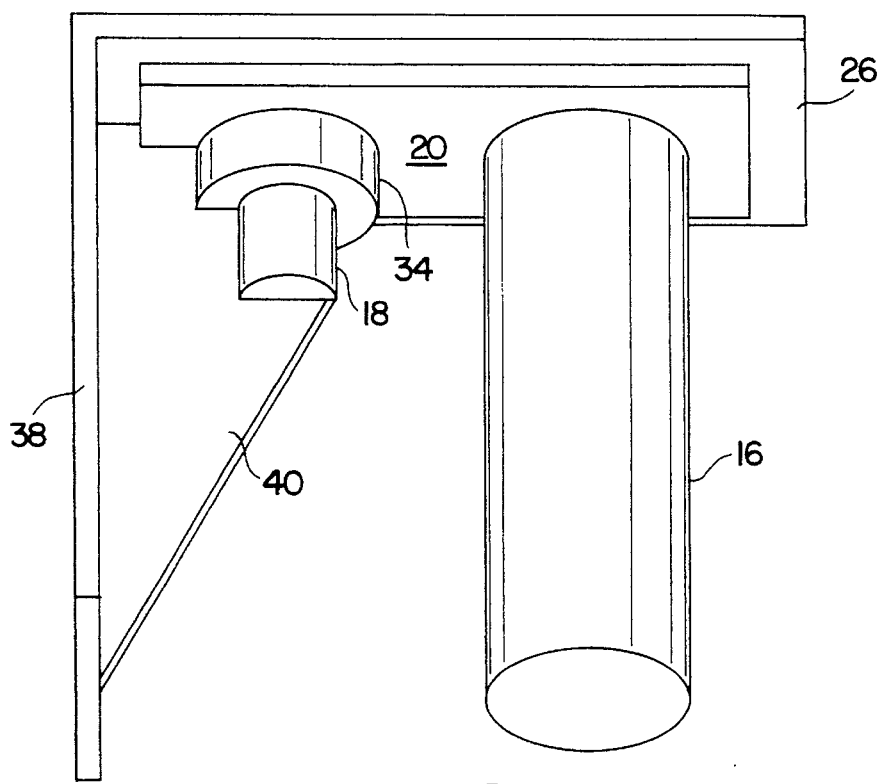
FIG. 2 is a view from the underside of FIG. 1.

Referring now to FIGS. 1–4, inclusive, a package 10 for a dental implant 12 and a related component 14 has two separate compartments 16 and 18, for containing the implant and the related component, respectively. Each compartment has a top opening 22, 24, respectively through a common substantially planar support 20. The support 20 is recessed in a peripheral frame 26, to which a cover 28 can be peripherally attached. The implant 12 is held in a sleeve 36 which in turn is supported within the top portion of the first compartment 16, extending from the opening 22 part way into this compartment. The sleeve 36 may have a preferably slot-like aperture (not shown) along the side to provide a view of the implant 12. Generally according to current practice the implant is made of titanium or a dilute alloy of titanium, and the sleeve 36 is made of the same material. In the present invention the sleeve is shorter than the implant, as appears in FIG. 1. The related component 14, which as here illustrated is a cover screw for the implant, is held in the second compartment 18, which is provided with a widened top portion 34 for the head of the cover screw. A side panel 38 is connected end-wise to the frame 26. These parts 26 and 38 may be rectangularly connected, as shown. A buttress panel 40 is peripherally joined to the side panel and the second compartment.

Referring now to FIG. 5, a container 50 has a pocket 52 adapted to receive the implant package 10, lying on a side as shown. The container 50 has a relatively stiff frame 54 around the pocket, and a removable cover 56 which is adapted to be attached to the frame. The parts 12 and 14 are first sealed in the implant package 10, which is then sealed in the container 50. This packaging structure provides a double seal for parts which are sterile, in which the parts can safely be stored, transported and delivered to a user with sterility and structure intact. When preparing to place the implant in a patient, the dental practitioner will first remove the implant package 10 from the container 50. Then, by merely removing the cover 28 from the implant package, the practitioner will have the implant prepared for placement, without removing it from the container 10 until ready to place it.

In FIG. 6 the two parts 12 and 14 are assembled into a unit for storage, transportation and delivery. An implant package 66 has a screw-on cap 64. A holder 62 for the assembled unit 12, 14 has means 68 to grasp the head 32 of the cover screw 14. The holder has a shoulder 70 which stops against the top 72 of the package 66 and is surrounded by the cap 64 which when screwed down on the package holds the shoulder 70 against the stop 72. The implant 12 and attached cover screw 14 are thereby held within the package 66. To access the implant and its cover screw the cap 64 is unscrewed and the holder 62 is grasped to remove them from the package. The head 32 is held by friction in the grasping means 68 of the holder, which can be used to carry the implant to a desired location, and can be removed as desired. In this embodiment of the invention the sleeve 36 is omitted.

In FIG. 7 the two parts 12 and 14 are carried separately, one in the container 86, and one in the screw-on cap 76. A titanium sleeve 84 in the top part of the container encloses the implant 12, like the sleeve 36 as in FIG. 1. When screwed down the cap 76 presses the implant against a stop 82 at the top of the sleeve. A compartment 78 is provided in the cap, similar to the compartment 18, 34 in FIG. 1, for receiving the cover screw 14 and its head 32. A removable plug 74 in the top of the cap holds the cover screw in place in the cap until it is needed.

The container 50 can be modified to provide a double seal for the embodiments shown in FIGS. 6 and 7.

The compartments 16, package 66 and package 86 may be furnished with scalar markings, e.g: notch 90 in FIGS. 1 and 7, to indicate the length of the implant 12 contained in it.

We claim:

1. In combination an elongated surgical implant fixture having a head end and a tail end and capsule means enclosing said implant fixture, comprising:

an elongated tubular housing having a first end and a second end, said first end being opened and said second end being closed, said housing having a length longer than said implant fixture, said housing for receiving a portion of said implant fixture;

stop means at said first end for stopping said head end from penetrating into said housing;

cap means for closing said first end closely overlying said head end and for holding said head end substantially fixed with relation to said stop means with said tail end spaced from said closed end; and a tubular liner made of substantially the same material as said implant fixture, said liner fixed within said housing and extending along an interior wall surface of said housing from said first end toward said second end for enclosing at least a part of said implant fixture when said implant fixture is present in said housing.

2. A combination according to claim 1 including marker means on said housing for indicating the length of an implant fixture enclosed therein.

3. A combination according to claim 1 in which said liner includes said stop means.

4. A combination according to claim 3 in which said cap means includes means to engage said head end against said stop means.

5. A combination according to claim 4 wherein said implant fixture is generally cylindrical and said head end has a larger diameter than the remainder of said implant fixture, said stop means including an annular surface surrounding said first end and said engaging means of said cap means pressing said head end against said annular surface.

6. A combination according to claim 1 in which said liner is made of titanium or a dilute alloy of titanium.

7. A combination according to claim 1 in which said housing is transparent and said liner is opaque.

8. A combination according to claim 1 in which said housing has an annular end-wall at said first end and said liner has at one end a flange overlying said end-wall when said liner is fitted within said housing.

9. A combination according to claim 8 wherein said implant fixture is generally cylindrical and said head end has a larger diameter than the remainder of said implant fixture, and wherein said flange is said stopping means.

10. A combination according to claim 9 including means to hold said head end against said flange when said implant fixture is inserted tail-end first through said liner into said housing.

11. A combination according to claim 10 wherein said cap means includes means for pressing said head end against said flange when said cap means is fixed to said housing.

12. In combination an elongated surgical implant fixture made of a specified material and having a head end and a tail end, and a capsule for enclosing said implant fixture, comprising:.

an elongated tubular housing having a first end, a second end, and a length longer than said implant fixture, said first end being open and said second end being closed, said housing for receiving said implant fixture;

a tubular liner made of said specified material fixed within said housing and extending along an interior wall surface thereof from said first end toward said second end, said liner for enclosing at least part of said implant fixture when said implant fixture is present in said housing;

stop means at said first end for stopping said head end from penetrating into said liner; and means for closing said first end.

13. In combination an elongated surgical implant fixture having a head end and a tail end and a separate component for use therewith, and bicameral encapsulation means separately enclosing said implant fixture and said separate component, comprising:

a first elongated tubular capsule having a length longer than said implant fixture and a first substantially planar opening at one end, said first capsule for receiving a portion of said implant fixture;

stop means near said first opening for holding said head end of said implant fixture near said first opening, a second tubular capsule having a second substantially planar opening at one end, said second capsule for receiving said separate component through said second opening;

a support for said first and second capsules holding said first and second openings substantially in a common plane; and closure means in said common plane for covering said first and second openings, said closure means closely overlying said head end of said implant fixture.

14. A combination according to claim 13 in which said support lies in said common plane.

15. A combination according to claim 14 in which said first capsule is substantially tubular, said first opening is substantially circular, and an end of said first capsule opposite said first opening is closed.

16. A combination according to claim 15 in which said second capsule is substantially tubular, said second opening is substantially circular, and an end of said second capsule opposite said second opening is closed.

17. A combination according to claim 16 in which said first and second capsules extend in the same direction from said support.

18. A combination according to claim 17 in which said support includes a part extending laterally from said support in the same direction as said first and second capsules.

19. A combination according to claim 18 in which said part extends from an end of said support substantially alongside said second capsule.

20. A combination according to claim 19 in which said first capsule is longer than said second capsule.

21. A combination according to claim 19 including a substantially flat brace lying in a plane perpendicular to both said support and said part, said flat brace being connected to both said support and said part.

22. A combination according to claim 21 in which said brace is further connected to said second capsule.

23. A combination according to claim 13 in which said closure means includes a peelable sheet peripherally bonded to said support.

24. A combination according to claim 13 in which said first capsule is substantially tubular, said first opening is substantially circular, and an end of said first capsule opposite said first opening is closed.

25. A combination according to claim 24 in which said second capsule is substantially tubular, said second opening is substantially circular, and an end of said second capsule opposite said second opening is closed.

26. A combination according to claim 25 in which said first capsule is longer than said second capsule.

27. A combination according to claim 13 wherein said first capsule includes a closed end opposite said first opening and a tubular liner, said liner extending along an interior wall surface of said first capsule from said first opening toward said closed end, said first capsule for enclosing at least a part of said implant fixture when said implant fixture is present in said first capsule.

28. A combination according to claim 27 in which said stop means is positioned for stopping said head end from penetrating into said liner.

29. A combination according to claim 27 in which said liner is made of the same material as said implant fixture.

30. A combination according to claim 27 in which said first capsule is transparent and said liner is opaque.

31. A combination according to claim 27 in which said liner is made of titanium or a dilute alloy of titanium.

32. A combination according to claim 13 including marker means on said first capsule for indicating the length of an implant fixture enclosed in said first capsule.

33. A combination according to claim 13 wherein said implant fixture is generally cylindrical and said head end has larger diameter than the remainder of said implant fixture, and wherein said stop means includes an annular surface adjacent said first opening for engaging said head end.

34. A combination according to claim 13 in which said second capsule is dimensioned to enclose said separate component.

35. A combination according to claim 34 in which said component is a cover screw.

36. In combination, a bicameral encapsulation for a dental implant and an article intended for use with said implant, comprising;.

a first elongated substantially tubular capsule having a first end, a second end, and a length longer than said dental implant, said first end having a first substantially planar opening and said second end being closed, said dental implant having a substantially cylindrical body, a head end, and being housed within said first capsule, said head end having a diameter larger than said cylindrical body;

a second capsule having a second substantially planar opening, said article being housed within said second capsule;

support means for said first and second capsules holding said first and second openings in a substantially fixed spatial relation;

stop means within said first capsule for stopping said head end from penetrating into said first capsule; and removable cover means covering said first and second openings, said cover means closely overlying said head end.

37. A combination according to claim 36 in which said support means for holding said first and second openings in a common plane, and said cover means covers both said first and second openings in said common plane.

38. A combination according to claim 37 in which said cover means is a peelable sheet peripherally bonded to said support means.

39. A combination according to claim 37 in which said support means lies in said common plane.

40. A combination according to claim 39 in which said cover means is peripherally attached to said support means.

41. A combination according to claim 39 in which said cover means is a peelable sheet peripherally bonded to said support means.

42. A combination according to claim 36 in further combination with an enclosure having a recess for receiving said bicameral encapsulation and second removable cover means for said recess.

43. A combination according to claim 42 in which said recess has an opening peripherally surrounded by a flange and said second cover means is sealable to said flange.

44. In combination an elongated surgical implant fixture having a head end, a tail end and threads extending most of the length therebetween, and a package for encasing said surgical implant fixture, comprising:

a first elongated capsule having a first end, a second end, and an interior wall disposed between said first and second end, said first end being opened and said second end being closed, said first capsule for receiving a portion of said implant fixture;

a liner fixed within said first elongated capsule and extending along said interior wall, said liner having an upper portion adjacent said first end;

stop means on said liner for prohibiting said tail end of said implant fixture from contacting said second end of said first elongated capsule; and covering means for covering said first end of said first capsule, said covering means closely overlying said head end of said implant fixture.

45. The combination according to claim 44, wherein said covering means further includes means for maintaining said head end of said implant fixture in a fixed relation to said stop means, said maintaining means engaging said head end of said implant fixture.

46. The combination according to claim 44, wherein said stop means is positioned on said upper portion of said liner.

47. The combination according to claim 44, wherein said liner has a length that is less than the length of said implant fixture.

48. The combination according to claim 44, wherein said stop means directly engages said head end of said implant fixture.

49. The combination according to claim 44, wherein said covering means includes a peelable sheet.

50. The combination according to claim 44, further including a second capsule and a support, said first capsule and said second capsule extending from said support, said second capsule having a third end and a fourth end, said third end being opened and said fourth end being closed, said second capsule for receiving and enclosing a part cooperating with said implant fixture.

51. The combination according to claim 50, wherein said covering means further covers said third end of said second capsule.

52. The combination according to claim 50, further including a frame connected to a periphery of said support.

53. The combination according to claim 52, further including a side panel connected to and extending from said frame in a direction generally perpendicular to said frame.

54. The combination according to claim 53, further including a buttress panel connecting a portion of said side panel to a portion of said second capsule.

55. The combination according to claim 50, wherein said first capsule and said second capsule extend in the same direction from said support.

56. The combination according to claim 50, wherein said first capsule is longer than said second capsule.

57. The combination according to claim 44, wherein said implant fixture is made of titanium or a dilute alloy of titanium.

58. The combination according to claim 57, wherein said liner is made of titanium or a dilute alloy of titanium.

59. The combination according to claim 44, in combination with an enclosure having a recess for receiving said package and removable cover means for covering said recess when said package is disposed therein.

60. A package for encasing an implant fixture, said implant fixture having a head end and a tail end, said package comprising:
- a first elongated capsule having a first end, a second end, and an interior wall disposed between said first and second end, said first end being opened and said second end being closed, said first capsule for receiving a portion of said implant fixture;
- a liner fixed within said first elongated capsule and extending along said interior wall, said liner having an upper portion adjacent said first end;
- stop means on said liner for prohibiting said tail end of said implant fixture from contacting said second end of said first elongated capsule; and
- covering means for covering said first end of said first capsule, said covering means including a peelable sheet.

61. A package for encasing a implant fixture, said implant fixture having a head end and a tail end, said package comprising:
- a first elongated capsule having a first end, a second end, and an interior wall disposed between said first and second end, said first end being opened and said second end being closed, said first capsule for receiving a portion of said implant fixture;
- a second capsule for receiving a part cooperating with said implant fixture, said second capsule having a third end and a fourth end, said third end being opened and said fourth end being closed;
- a support from which said first capsule and said second capsule extend;
- a liner fixed within said first elongated capsule and extending along said interior wall, said liner having an upper portion adjacent said first end;
- stop means on said liner for prohibiting said tail end of said implant fixture from contacting said second end of said first elongated capsule; and
- covering means for covering said first end of said first capsule.

62. The package according to claim 61, wherein said covering means further covers said third end of said second capsule.

63. The package according to claim 61, further including a frame connected to a periphery of said support.

64. The package according to claim 63, further including a side panel connected to and extending from said frame in a direction generally perpendicular to said frame.

65. The package according to claim 64, further including a buttress panel connecting a portion of said side panel to a portion of said second capsule.

66. The package according to claim 61, wherein said first capsule and said second capsule extend in the same direction from said support.

67. The package according to claim 61, wherein said first capsule is longer than said second capsule.

68. A device for encasing a implant fixture having a head end and a tail end, said encasing device comprising:
- a package including
  - a first elongated capsule having a first end, a second end, and an interior wall disposed between said first and second end, said first end being opened and said second end being closed, said first capsule for receiving a portion of said implant fixture,
  - a liner fixed within said first elongated capsule and extending along said interior wall, said liner having an upper portion adjacent said first end,
  - stop means on said liner for prohibiting said tail end of said implant fixture from contacting said second end of said first elongated capsule, and
  - covering means for covering said first end of said first capsule; and
- an enclosure having a recess for receiving said package; and
- removable cover means for covering said recess when said package is disposed therein.

69. The encasing device according to claim 68, wherein said package further includes a second capsule for receiving a part cooperating with said implant fixture.

* * * * *